United States Patent [19]
Leviness et al.

[11] Patent Number: 5,817,701
[45] Date of Patent: Oct. 6, 1998

[54] SLURRY HYDROCARBON SYNTHESIS WITH CYCLIC CO PURGE AND CATALYST REJUVENATION

[75] Inventors: Stephen C. Leviness, Baton Rouge, La.; Willard N. Mitchell, Ridgeland, Miss.

[73] Assignee: Exxon Research and Engineering Company, Florham Park, N.J.

[21] Appl. No.: 850,565

[22] Filed: May 2, 1997

[51] Int. Cl.⁶ .................................................... C07C 27/00
[52] U.S. Cl. ........................... 518/700; 518/705; 502/21; 502/22; 502/53; 502/765
[58] Field of Search .................. 502/21, 53, 22, 502/765; 518/700, 705

[56] References Cited

U.S. PATENT DOCUMENTS

| | | | |
|---|---|---|---|
| 5,157,054 | 10/1992 | Herbolzheimer et al. | 518/700 |
| 5,260,239 | 11/1993 | Hsia | 502/30 |
| 5,268,344 | 12/1993 | Pedrick et al. | 502/30 |
| 5,283,216 | 2/1994 | Mitchell | 502/30 |
| 5,292,705 | 3/1994 | Mitchell | 502/325 |
| 5,348,982 | 9/1994 | Herbolzheimer et al. | 518/700 |
| 5,545,674 | 8/1996 | Behrmann et al. | 518/715 |

FOREIGN PATENT DOCUMENTS 2299767  10/1996  United Kingdom.

*Primary Examiner*—Gary Geist
*Assistant Examiner*—J. Parsa
*Attorney, Agent, or Firm*—Jay Simon

[57] ABSTRACT

Partially deactivated catalyst in a slurry hydrocarbon synthesis process is rejuvenated employing a cyclic rejuvenation process in which syngas or CO flow into the slurry is stopped to stop the hydrocarbon synthesis reaction, the CO purged out of the slurry with a purge gas in the presence of hydrogen, the catalyst rejuvenated with a hydrogen containing rejuvenating gas and the hydrocarbon synthesis reaction restarted by passing the synthesis gas feed back into the reactor. All or a portion of the purge gas and/or the rejuvenating gas may be recycled during the respective purge and/or rejuvenation. The hydrogen required during the purge is typically part of the purge gas.

20 Claims, 2 Drawing Sheets

SLURRY HYDROCARBON SYNTHESIS WITH CYCLIC CO PURGE AND CATALYST REJUVENATION

BACKGROUND OF THE DISCLOSURE

1. Field of the Invention

The invention relates to a process for rejuvenating solid catalyst particles in a hydrocarbon slurry. More particularly, the invention relates to a slurry hydrocarbon synthesis process in which the slurry is periodically purged of CO, followed by passing catalyst rejuvenating gas through the slurry to restore catalyst activity. Both the purge and rejuvenating gasses may be recycled after removing catalyst deactivating species.

2. Background of the Invention

Slurry hydrocarbon synthesis (HCS) processes are known. In a slurry HCS process a synthesis gas (syngas) comprising a mixture of $H_2$ and CO is bubbled up as a third phase through a slurry in a reactor in which the slurry liquid comprises hydrocarbon products of the synthesis reaction and the dispersed, suspended solids comprise a suitable Fischer-Tropsch type hydrocarbon synthesis catalyst. Reactors which contain such a three phase slurry are sometimes referred to as "bubble columns", as is disclosed in U.S. Pat. No. 5,348,982. Irrespective of whether the slurry reactor is operated as a dispersed or slumped bed, the mixing conditions in the slurry will typically be somewhere between the two theoretical limiting conditions of plug flow and back mixed. Syngas made from hydrocarbon feedstocks which contain nitrogen (i.e., natural gas) or nitrogen containing compounds (i.e., resids, coal, shale, coke, tar sands, etc.) invariably contains HCN and $NH_3$ which contaminate the reactive slurry and rapidly, but reversibly, deactivate the catalyst. Certain oxygenates and carbonaceous compounds which are formed in the slurry as by-products of the HCS reaction are also believed to cause rapid deactivation. Deactivation of such catalysts by these species is reversible and catalytic activity is restored (the catalyst rejuvenated) by contacting the deactivated catalyst with hydrogen. The activity of the HCS catalyst in the reactive slurry may be intermittently or continuously rejuvenated by contacting the slurry with hydrogen or a hydrogen containing gas to form a catalyst rejuvenated slurry as is disclosed, for example, in U.S. Pat. Nos. 5,283,239; 5,268,344, and 5,283,216. UK patent publication GB 2, 299,767A relates to a batch mode of catalyst rejuvenation in a filly backmixed, continuous stirred tank reactor. However, this process is disclosed as requiring a regeneration time of from 12 to 24 hours every 3–5 days.

SUMMARY OF THE INVENTION

The invention relates to a process for rejuvenating a hydrocarbon synthesis (HCS) catalyst in-situ in a CO containing HCS slurry, by first purging the CO out of the slurry with a hydrogen containing purge gas and then passing a hydrogen containing catalyst rejuvenating gas through the purged slurry, until the desired degree of catalyst rejuvenation has occurred. The slurry is a three phase, Fischer-Tropsch type slurry comprising catalyst particles and gas bubbles in a hydrocarbon slurry liquid. The slurry liquid comprises hydrocarbon products of the HCS reaction which are liquid at the reaction conditions and the gas bubbles present in the slurry prior to the purge comprise unreacted synthesis gas (syngas) and gas products of the HCS reaction. The process of the invention is a cyclic or periodic batch process, as the hydrocarbon synthesis reaction is substantially stopped during the CO purge by ceasing the flow of syngas or CO into the slurry. The syngas comprises a mixture of $H_2$ and CO. In a preferred embodiment, the flow of CO into the slurry is not renewed until the catalyst has been rejuvenated, irrespective of the source of CO. The amount of time required to stop the CO flow into the HCS reactor, purge remaining CO out of the slurry, rejuvenate the catalyst and bring the reactor back on-line into a hydrocarbon production mode depends on whether or not the purge and/or rejuvenation are once through, recycle or combination. For a once through mode, the purge may be achieved in a matter of from 2–5 minutes. Subsequent once through rejuvenation of the catalyst can be achieved within 10 minutes, whereas for both recycle purge and recycle rejuvenation, the recycle purge will typically be accomplished within about 45 minutes and the recycle rejuvenation will typically be achieved within about 30 minutes. By recycle is meant that at least a portion of the respective gas, whether purge or rejuvenating gas, and preferably a majority of the gas passed through the slurry is recycled back into the slurry during the purge or rejuvenation. However, for the case of recycled rejuvenating gas, the catalyst rejuvenation produces a rejuvenation product gas (offgas) which contains catalyst deactivating species. These species are removed from the gas with water before the gas is recycled back into the slurry during rejuvenation, to avoid recontamination and deactivation of the catalyst being rejuvenated in the slurry. The choice is determined by gas availability, cost and desired reactor productivity. For example, both once through purge and rejuvenation take the least amount of time, but require the greatest gas use (including the $H_2$), since the gas isn't recycled back into the slurry. Recycling both the purge and rejuvenating gas requires more time, but requires the least amount of makeup gas, including $H_2$. In this case, both the purge and rejuvenating gasses may require preheating to avoid too great a slurry temperature drop, whereas the once through mode for both purge and rejuvenation may require no preheating of the gasses. The time required for a once through purge with recycled rejuvenating gas lies in between the other two. Irrespective of the mode, the purge and rejuvenation time required for any of the purge and rejuvenation embodiments of the invention will be less than the 12–24 hours required for the process disclosed in UK patent publication GB 2,299,767A and this time difference is important to the successful operation of a commercial size HCS reactor. During purge and rejuvenation, the reactor is not producing hydrocarbons and the slurry temperature will drop due to the absence of the exothermic HCS reaction. The longer the purge and rejuvenation take, the more will be the heat required to be added to the slurry to prevent cooling. While some of this heat may be added by means of heat exchangers and pipes in the reactor, a facile alternative is to heat the purge and rejuvenating gas before they are passed into the slurry in the reactor.

The CO purge is accomplished using a purge gas which contains sufficient hydrogen to prevent catalyst deactivation. Useful purge gas includes, for example, a mixture of $H_2$ and a diluent gas, such as $N_2$, $CH_4$, and the like. A plentiful supply of nitrogen may be available if HCS plant has a cryogenic oxygen generating unit to provide oxygen for syngas generation. It is important in a commercial size reactor, that the volumetric gas flow up through the slurry during the CO purge and subsequent rejuvenation be sufficient to maintain the catalyst particles dispersed and suspended in the slurry, so that they remain in contact with hydrogen to prevent deactivation. This deactivation, if it occurs, is not fully reversible. This flow rate is typically substantially less than that required to prevent weeping of the catalyst down through the gas injection means at the bottom of the slurry. Preventing this catalyst weeping down through the gas distributor will normally determine the minimum required gas flow rate into the reactor and this minimum rate is typically greater than the gas flow rate required to maintain the gas particles suspended and dispersed in the slurry liquid, but less than that required for the desired hydrocarbon synthesis in the reactor. Therefore, it is inefficient to use all or mostly hydrogen for the purge and rejuvenation, unless the gas containing the unreacted hydrogen which is passed through the slurry can be recycled and fed back into the bottom of the slurry again. If a diluent gas such as nitrogen, methane and the like are not available in sufficient quantity, other gasses can be used, such as process gas which doesn't adversely effect the slurry components or subsequent rejuvenation. Recycled tail gas from an HCS reactor comprising, for example, $N_2$, $CH_4$, $CO_2$, and the like, along with minor amounts of CO containing, unreacted syngas may be used. If CO is present in the purge gas, the amount of CO should be less than 10 mole %, preferably less than 5 mole %, and hydrogen must be present in an amount such that the $H_2$ to CO ratio is greater than 3:1, preferably greater than 4:1 and more preferably greater than 5:1. It is preferred that the purge gas not contain any CO and that just about all the CO be removed from the slurry prior to rejuvenation. Therefore, if a CO containing gas, such as an HCS reactor tail gas or other CO containing gas is used as a purge gas, it is preferred to remove the CO from the gas before it is introduced into the slurry as all or part of the purge gas. This can be accomplished by adsorption, by chemical scrubbing, by passing the gas through a water gas shift reactor, and the like. The CO can be purged from the reactor in a matter of minutes, at which time the catalyst rejuvenating gas in passed into the slurry. Further, while it is also preferred that all of the CO be removed from the slurry by the purge, a small amount (e.g., <10 volume %) may remain, it being understood that any CO remaining will be removed by reacting with the $H_2$ in the rejuvenating gas, thereby preventing catalyst rejuvenation until all the CO is consumed.

The catalyst rejuvenating gas comprises hydrogen, typically with one or more diluent gasses to insure that the catalyst particles are kept suspended and to prevent catalyst weeping down through the gas injectors as mentioned above, and may be the same gas used for the purge. During catalyst rejuvenation, the hydrogen containing rejuvenating gas is bubbled up through the purged slurry in which the hydrogen contacts the reversibly deactivated catalyst particles and rejuvenates the catalyst. In most cases complete, or almost complete restoration of catalytic activity is accomplished. The amount of hydrogen present in the rejuvenating gas will typically be sufficient to insure that the rejuvenation product gas contains unreacted hydrogen, to insure that catalyst particles throughout the slurry remain in contact with hydrogen. This unreacted hydrogen is useful and may be recovered and recycled back into the reactor ELs part of the rejuvenating gas after treatment, burned as fuel or in a flare, or sent back to the syngas generation. Depending on the $H_2$ concentration in this offgas, it is preferred that this gas be recycled back into the slurry for rejuvenation after catalyst deactivating species have been removed. The rejuvenation produces a gas product (rejuvenation offgas) of the catalyst rejuvenation reaction which contains catalyst deactivating species. These species, which comprise mainly $NH_3$, are water removable and are removed by scrubbing the gas with water, before passing it back into the slurry as part of the rejuvenating gas. The amount of unreacted hydrogen present in the offgas depends on its concentration in the rejuvenating gas and can vary, for example, from about 3–50 or more mole %.

Thus, the process of the invention comprises (a) stopping the flow of CO into the HCS slurry, (b) passing a purge gas and $H_2$ through the slurry to remove CO and produce a CO reduced slurry, (c) passing an $H_2$ containing rejuvenating gas through the CO reduced slurry to at least partially rejuvenate the catalyst particles and form a rejuvenated catalyst slurry, and then (d) passing a mixture of $H_2$ and CO into the rejuvenated catalyst slurry to resume hydrocarbon synthesis. During the purge, the $H_2$ may be mixed with the purge gas or it may be introduced into the slurry separate from the purge gas. In most cases it is more convenient for the purge gas to contain the $H_2$. While it is preferred to completely stop the CO flow into the slurry, some CO may still flow into the slurry and the process of the invention will still be effective as long as the total CO content of the total gas entering the slurry is less than 10 mole % and preferably less than 5 mole % and the total $H_2$ to CO ratio is greater than 3:1, preferably greater than 4:1 and more preferably greater than 5:1. However, the CO will be wasted by conversion primarily into methane, with rejuvenation taking more time and/or requiring greater amounts of $H_2$ in the rejuvenating gas. Therefore, in the context of the practice of the invention, while the term "stopping the flow of CO" is meant to include permitting the above amount of CO to flow into the slurry, in a preferred embodiment it is meant in it's literal sense. In a further embodiment, at least a portion of the hydrogen-containing offgas produced during the catalyst rejuvenation, and which contains water removable catalyst deactivating species produced by the rejuvenation reaction, is contacted with water (e.g., scrubbed) to remove these species from the gas and is recycled back into the slurry as part of the rejuvenating gas. In a more specific embodiment, the process of the invention relates to a slurry HCS process which comprises the steps of:

(a) passing a synthesis gas comprising a mixture of $H_2$ and CO into a hydrocarbon synthesis slurry in the presence of one or more catalyst deactivating species and a hydrocarbon synthesis catalyst at reaction conditions effective to form hydrocarbons from said gas, at least a portion of which are liquid at said reaction conditions, wherein said slurry comprises said catalyst and gas bubbles in a hydrocarbon slurry liquid comprising said liquid hydrocarbons, and wherein said species at least partially reversibly deactivate said catalyst and form a deactivated catalyst slurry during said reaction;

(b) stopping the flow of CO into said slurry;

(c) passing a purge gas and $H_2$ through said slurry to remove CO and form a CO reduced slurry in which said CO content is less than 10 mole % and preferably less than 5 mole % of said gas in said slurry;

(d) passing a catalyst rejuvenating gas comprising $H_2$ through said CO reduced slurry to at least partially rejuvenate said deactivated catalyst and form a rejuvenated catalyst slurry, and (e) passing synthesis gas back into said rejuvenated slurry to produce hydrocarbons.

Further embodiments include recycling all or a portion of the purge gas and/or the rejuvenating gas back into the slurry. The added $H_2$ passed through the slurry in step (c) may be part of the purge gas. If the rejuvenating gas is recycled, it is scrubbed with water, etc. as above, before it is passed back into the slurry Yet another embodiment includes preheating all or a portion of the purge gas and/or rejuvenating gas before it is passed into the slurry. In an embodiment in which multiple HCS stages are employed, tail gas from one or more stages downstream of the first stage may be used as purge gas and as rejuvenating gas, provided the mole ratio of the $H_2$ to CO in the gas is >3:1, preferably >4:1, and more preferably >5:1, and the CO content of the gas is below about 10 mole % if it is used as purge gas. Adjustment of the $H_2$ to CO ratio and the CO content can be achieved by CO removal using known methods and/or $H_2$ addition.

DETAILED DESCRIPTION

Figure 1:
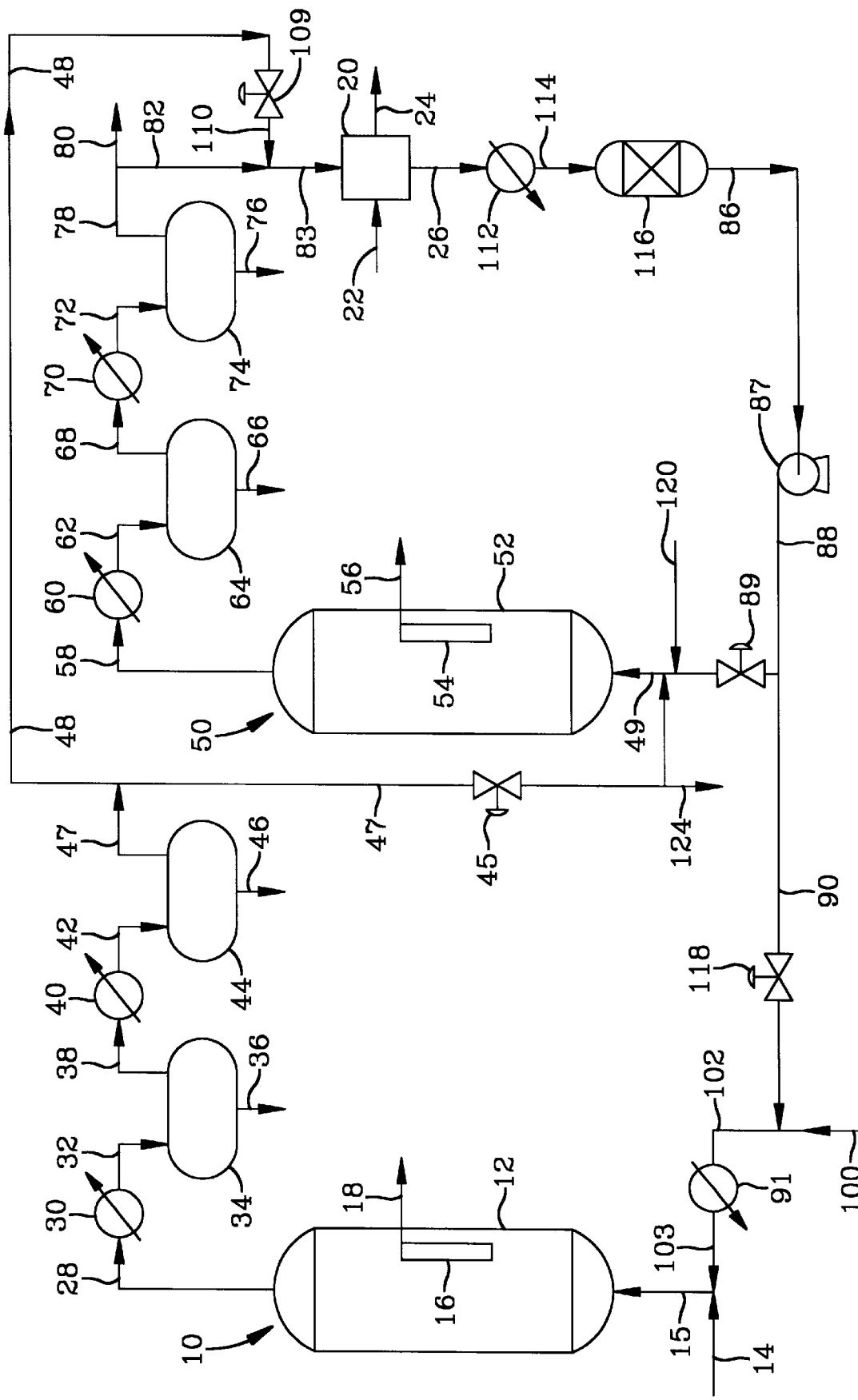
FIG. 1 is a box type schematic of an HCS process of the invention without hot and cold separators dedicated to the rejuvenation.

In a Fischer-Tropsch slurry HCS process, a syngas comprising a mixture of $H_2$ and CO is bubbled up into a reactive HCS slurry in which it is catalytically converted into hydrocarbons and preferably liquid hydrocarbons. The mole ratio of the hydrogen to the carbon monoxide may broadly range from about 0.5 to 4, but which is more typically within the range of from about 0.7 to 2.75 and preferably from about 0.7 to 2.5. The stoichiometric mole ratio for a Fischer-Tropsch HCS reaction is 2.0, but there are many reasons for using other than a stoichiometric ratio as those skilled in the art know and a discussion of which is beyond the scope of the present invention. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_5+-C_{200}$) and preferably $C_{10+}$ paraffins, in a slurry HCS process employing a catalyst comprising a supported cobalt component include, for example, temperatures, pressures and hourly gas space velocities in the range of from about 320°–600° F., 80–600 psi and 100–40,000 V/hr/V, expressed as standard volumes of the gaseous CO and $H_2$ mixture (°C., 1 atm) per hour per volume of catalyst, respectively. Slurry catalyst rejuvenation conditions of temperature and pressure are similar to those for hydrocarbon synthesis and are disclosed in the prior art. The syngas may be formed by various means known to those skilled in the art, such as a fluid bed syngas generating unit (FBSG) as is disclosed, for example, in U.S. Pat. Nos. 4,888,131 and 5,160,456. This need not be further explained. Irrespective of the source, syngas typically contains catalyst deactivating species such as $NH_3$ and HCN. As the prior art teaches, deactivation by these species is reversible and the catalyst can be rejuvenated by contacting it with hydrogen. This restoration of the catalytic activity of a reversibly deactivated catalyst is referred to as catalyst rejuvenation. Catalyst deactivation is also caused by oxygenates and carbon precursors, some of which may be formed during the HCS process. Irrespective of the source or concentration of the reversible catalyst deactivating species, rejuvenation is periodically required to restore the activity of the catalyst. The catalyst will be rejuvenated whenever its activity, measured in terms of CO conversion to hydrocarbon products, falls to a predetermined level (e.g., 85–90%) with respect to that of fresh catalyst. While it is possible to rejuvenate the catalyst when its activity falls anywhere within the range of from about 50–95%, it will more typically be rejuvenated when the activity falls to a value between 85–90%. The rejuvenation frequency depends on the level of deactivating species in the syngas feed. During rejuvenation, these species (e.g., $NH_3$ and HCN, and primarily $NH_3$) are formed and removed as part of the gas products of the rejuvenation reaction (rejuvenation offgas). In a preferred embodiment, the rejuvenating gas contains sufficient $H_2$ for the offgas to contain appreciable amounts of unreacted $H_2$ which can be recycled back into the slurry for rejuvenation. However, the presence of catalyst deactivating species requires the offgas to be contacted with water to remove the catalyst deactivating species from the gas. Such contacting or scrubbing is easily achieved by passing the gas through a venturi scrubber, a packed column and the like.

The process of the invention may be conducted under shifting or non-shifting conditions during rejuvenation, although non-shifting conditions are preferred. Shifting will occur if CO is present in the rejuvenating gas and if the amount of $CO_2$ present is less than 5–10 mole %. By shifting is meant a water gas shift reaction in which CO reacts with water vapor to produce $H_2$ and $CO_2$. While the conditions for suppressing a water gas shift reaction will depend somewhat on the particular HCS catalyst being rejuvenated, in general these conditions include (i) a temperature of no more than about 250° C., (ii) the substantial absence of CO, or (iii) $CO_2$ present in an amount sufficient to prevent the shift reaction (i.e., >5 mole % and preferably >10 mole %) in the rejuvenating tail gas. Typical commercial syngas feeds contain at least 2–3 mole %, and more usually 5–10 mole % $CO_2$, unless $CO_2$ removal prior to hydrocarbon syntheses is practiced, although this is usually not economical. The presence of this much $CO_2$ will generally prevent water gas shift from occurring over Co catalysts, except at very high temperatures (e.g., >500° F.). This is based on studies conducted with a commercial size slurry HCS reactor which cannot be predicted or duplicated by the use of laboratory equipment. Typical commercial syngas feeds contain at least 2–3 mole %, and more usually 5–10 mole % $CO_2$, unless $CO_2$ removal prior to hydrocarbon syntheses is practiced, although this is usually not economical. The presence of this much $CO_2$ will generally prevent water gas shift from occurring over Co catalysts, except at very high temperatures (e.g., >500° F.). Thus, in yet another embodiment, the invention relates to a process for reducing and preferably preventing a water gas shift reaction during the catalyst rejuvenation process, by conducting the rejuvenation in the presence of $CO_2$ in an amount sufficient to suppress the water gas shift reaction. A commercial slurry HCS reactor will typically be 20 or more feet high and 5 or more feet in diameter, with temperatures and reactant concentrations varying from top to bottom. It is not a backmixed system to the extent of a CSTR.

UK patent publication GB 2,299,767A discloses a periodic batch rejuvenation process in a CSTR laboratory reactor, in which the amount of hydrogen in the synthesis gas is slightly increased from an $H_2$ to CO ratio of 2:1 or 2:1, up to 2.15:1 and the syngas flow into the reactor is decreased, so that all of the CO is consumed. In contrast and by way of an illustrative, but nonlimiting example, for a slurry HCS reactor containing a supported Co metal catalyst in a hydrocarbon slurry liquid, the stoichiometric $H_2$ to CO mole ratio is 2.1:1. Even at a mole ratio of, e.g., 2.2, 2.5 or 2.9:1, all of the CO is not consumed by the HCS reaction in a commercial size reactor, unless the feed flow rate of synthesis gas is very low; the temperature is very high, and/or substantial water gas shift reaction occurs to consume CO while producing $H_2$. Therefore, gas having these low $H_2$ to CO mole ratios cannot be used for catalyst rejuvenation in a commercial size reactor. Further, the fully backmixed conditions in a CSTR laboratory reactor in which the temperature and reactant concentrations are constant throughout cannot be applied to a commercial size slurry HCS reactor, in which the syngas concentration decreases and the gas products of the HCS reaction increase as the gas bubbles rise up through the slurry. While it is possible, as a practical matter, 100% CO conversion typically is not achieved in a commercial size reactor, unless the $H_2$ to CO ratio is very high (e.g., at least >3:1). A high ratio favors the undesired formation of methane and hydrogenolysis of the valuable liquid hydrocarbons formed by the synthesis reaction. Commercial size reactors are typically designed for a synthesis gas flow rate in a range based on a desired hydrocarbon production. If this flow rate is decreased enough for all the CO to be consumed, catalyst attrition and weeping down through the gas distributor will occur. Therefore, the teaching of this patent publication is not applicable to either the process of the present invention or a commercial size HCS reactor.

FIG. 1 is a schematic block diagram of a two stage slurry hydrocarbon synthesis process according to one embodiment of the invention, in which the CO flow into the HCS reactors is periodically stopped, CO purged from the slurry, rejuvenating gas passed up through the slurry to rejuvenate the catalyst and the CO flow into the slurry resumed. The first stage slurry reactor 10 comprises a cylindrical vessel 12 which contains an HCS slurry (not shown) within. A syngas feed line 14 passes a syngas comprising a mixture of $H_2$ and CO into the bottom of the reactor via line 15 from where it is injected up into the bottom of the slurry as bubbles by suitable gas injection means (not shown) and reacts with the solid catalyst particles in the slurry liquid to form hydrocarbons, at least a portion of which are liquid at the reaction conditions. The liquid hydrocarbons are separated from the catalyst particles by suitable means, such as one or more filters either in the slurry in the reactor or in an outboard filtration vessel, as is known to those skilled in the art. In this particular embodiment, one or more liquid filters briefly illustrated as box 16 are immersed in the reactive slurry, with the liquid hydrocarbon products withdrawn from the reactor via line 18 and passed to further processing and upgrading into more valuable products, or sold neat. The syngas fed into the first stage reactor comprises a mixture of $H_2$ and CO. In a two or more stage HCS process, the first stage reactor or reactors are operated at less than 100% conversion (by conversion is meant the mole % CO in the syngas feed which reacts with the $H_2$ in the reactor) which results in unreacted syngas. The unreacted syngas and gas products of the HCS reaction pass up through the slurry into the top portion of the reactor and are withdrawn via gas product line 28 as tail gas. In a two stage hydrocarbon synthesis plant in which the tail gas from the first stage reactor(s) comprises the feed gas to the second stage reactor (s), the amount of syngas fed into the first stage reactor(s) and the CO conversion in the first stage must be such as to insure that the amount of unreacted syngas exiting the first stage in the tail gas is sufficient to supply the feed gas requirements to the second stage, with little and preferably no syngas make-up from the syngas plant. The first stage tail gas is passed through a first heat exchanger 30 in which it is cooled to condense some of the water vapor and $C_{10}$–$C_{12+}$ hydrocarbons out of the gas as liquids. The actual amounts and carbon numbers depend on the gas composition and the separator temperature and pressure. The mixture of condensed liquids and the remaining gas is passed via line 32 into separator 34 in which the liquids are removed from the bottom via line 36 and the gas removed overhead via line 38. Separator 34 is a hot separator and will typically operate at a temperature of from about 200° to 300° F. and a pressure between 200–600 psia.. The actual pressure is determined by the reactor pressure and the pressure drop associated with the gas lines and heat exchanger. It also depends on the catalyst in the reactor, as an iron based HCS catalyst may be used at 100–150 psia, whereas a cobalt catalyst runs more typically at 200–600 psia. The water and hydrocarbon reduced tail gas removed from separator 34 is passed through a second heat exchanger 40 via line 38 in which it is further cooled to condense most of the remaining water and heavier hydrocarbons from the gas, which are then passed into second separator 44 via line 42 from which the water and hydrocarbon condensate is removed via line 46, with the substantially water and $C_{5+}$ reduced tail gas fed into the bottom of second stage slurry HCS reactor 50 via gas feed lines 47 and 49, in which it is bubbled up through the bottom of the HCS slurry (not shown) in the reactor, in a manner much the same as for the first stage reactor. A typical temperature and pressure for the second stage separator may be in the 50°–150° F. range and a pressure of about 200–600 psia. The same considerations mentioned above for the pressure in hot separator 34 also apply here. The amount of water vapor remaining in the gas after the second stage or cold separation will typically be in the 0.2–0.5 mole % range. In the reactor 50, the $H_2$ and CO containing tail gas, contacts the catalyst particles in the slurry and at least a portion of the CO in the gas is converted into hydrocarbons, at least a portion of which are liquid at the reaction conditions. The second stage slurry reactor 50 also comprises a hollow outer shell 52 containing a three phase HCS slurry (not shown) and liquid filtration means 54 within, for separating the liquid hydrocarbon products from the catalyst particles as filtrate, with the filtrate removed from the reactor via line 56 and sent to further processing and upgrading to more useful products, etc.. Second stage reactor 50 is also operated at less than 100% CO conversion, which results in unreacted $H_2$ and CO exiting the reactor, along with the gas products of the HCS reaction, as part of the tail gas. The tail gas is removed overhead via gas line 58 and passed through a first or hot heat exchanger 60, in which some of the water and $C_{4+}$ hydrocarbon products are condensed to liquids. The gas and liquid mixture is passed from the first cooler 60 into first separator 64, via line 62. The liquids are removed from the bottom of the separator via line 66, and the water and hydrocarbon reduced tail gas is passed, via line 68, through a second or cold heat exchanger 70, which further cools the gas to condense most of the remaining water and heavier hydrocarbons to liquids. The gas and liquid mixture is passed into from second cooler 70 into second separator 74 via line 72, in which the liquids settle out of the gas and liquid mixture and are removed via line 76. The water and hydrocarbon reduced tail gas passes out of the separator 74 via line 78. As is the case for the gas removed from the first stage cold separator 44, the amount of water vapor typically remaining in the gas removed via line 78 will also be in the 0.2–0.5 mole % range.

When the catalyst activity in the first stage reactor 10 falls below anywhere from 50–95%, but for the sake of this illustration 90%, the flow of CO or syngas into the reactor is stopped and purge gas comprising a mixture of $H_2$ and a diluent such as $N_2$, or just a diluent, is passed up into and through the slurry in the reactor via lines 100, 102, 103 and 15, depending on whether or not $H_2$ continues to be fed into the reactor through lines 14 and 15 while the CO flow has been stopped. As discussed above under the Summary, other diluents such as $CH_4$ may also be used. All or a part of both the purge gas and the rejuvenation gas may also be a hydrogen rich hydroisomerization gas (e.g., primarily $H_2$ and $CH_4$), or other suitable and available process gas. If a hydrocarbon and water reduced second stage HCS tail gas is used, in the illustration shown in the Figure it is passed via lines 78, 82 and 83 through scrubber 20, in which it contacts water which removes the $NH_3$ and other water removable catalyst deactivating species. Water enters the scrubber via line 22 and an aqueous ammonia solution is removed via line 24. The hydrogen rich gas is passed from the scrubber, via line 26, through heat exchanger 112 which heats the gas, which is then passed via line 114 into a water gas shift reactor 116, in which it contacts a water gas shift reaction catalyst (not shown) to react the CO with remaining water vapor in the gas and form $H_2$ and $CO_2$, thereby reducing and preferably removing the CO from the tail gas and, at the same time increase the H2 content, before it is passed into the slurry as purge and/or rejuvenating gas. This $H_2$ containing and CO free tail gas exits the water gas shift reactor 116 via line 86, is compressed by compressor 87 and then fed, via lines 90, 102, 103 and 15 into the slurry in reactor 10 As all or part of the purge and/or rejuvenating gas. Heat exchanger 91, optionally heats the gas to maintain the slurry temperature in the reactor within the range of from about 350° to 550° F. during the purge and rejuvenation, depending on the catalyst type. For an iron based catalyst the temperature can be as high as 550° F., while for a cobalt based catalyst it will more typically run lower than 500° F. After the CO has been removed from the slurry, a catalyst rejuvenating gas, which in this embodiment will be the same as the purge gas, is passed into and up through the purged slurry via to rejuvenate the catalyst particles. In a still further embodiment, which is a preferred embodiment, the rejuvenating offgas, which contains appreciable quantities of $H_2$ (e.g., $\geq 10$ mole %) is removed during the rejuvenation as overhead and at least a portion is recycled back into the slurry as rejuvenating gas, by first passing it through the first stage hot and cold separators and then into the scrubber and shift reactor loop via lines 48, 110 and 83, etc.. During this time valve 109 is open, valve 45 is closed and syngas or first stage tail gas from another first stage HCS reactor is fed into the second stage HCS reactor as the HCS feed via lines 120 and 49, or via lines 88 and 49 while valve 89 is open. While the catalyst in the second stage reactor will occasionally need rejuvenating, the frequency rejuvenation frequency is far less than that in the first stage reactor 10, because almost all of the water removable catalyst deactivating species initially present in the syngas feed are removed by the two stage cooling and condensate separation between the two stages. Therefore, to rejuvenate the second stage catalyst, the flow of the $H_2$ and CO containing tail gas into reactor 50 is stopped and the tail gas is temporarily passed, via line 124 to other second stage HCS reactors (not shown), to syngas generation, used as fuel or burned in a flare. Purge gas is introduced into the slurry via lines 120 and 49 and will include the same possibilities and combinations as all of the embodiments disclosed above for the first stage reactor 10. The second stage rejuvenation offgas passes via line 58 through the second stage reactor tail gas hot and cold heat exchangers and separators, and then into the water scrubber and shift reactor loop via lines 78, 82 and 83. Not shown for the sake of convenience, is a heat exchanger between compressor 87 and reactor 50 for optionally heating the purge and/or rejuvenating gas being fed into the second stage reactor during purge and/or rejuvenation. Additionally, if desired, all or part of the purge and rejuvenating gas may be CO free tail gas recovered from another second stage reactor (not shown) and passed through the water gas shift reactor and then into the slurry in reactor 50.

Figure 2:
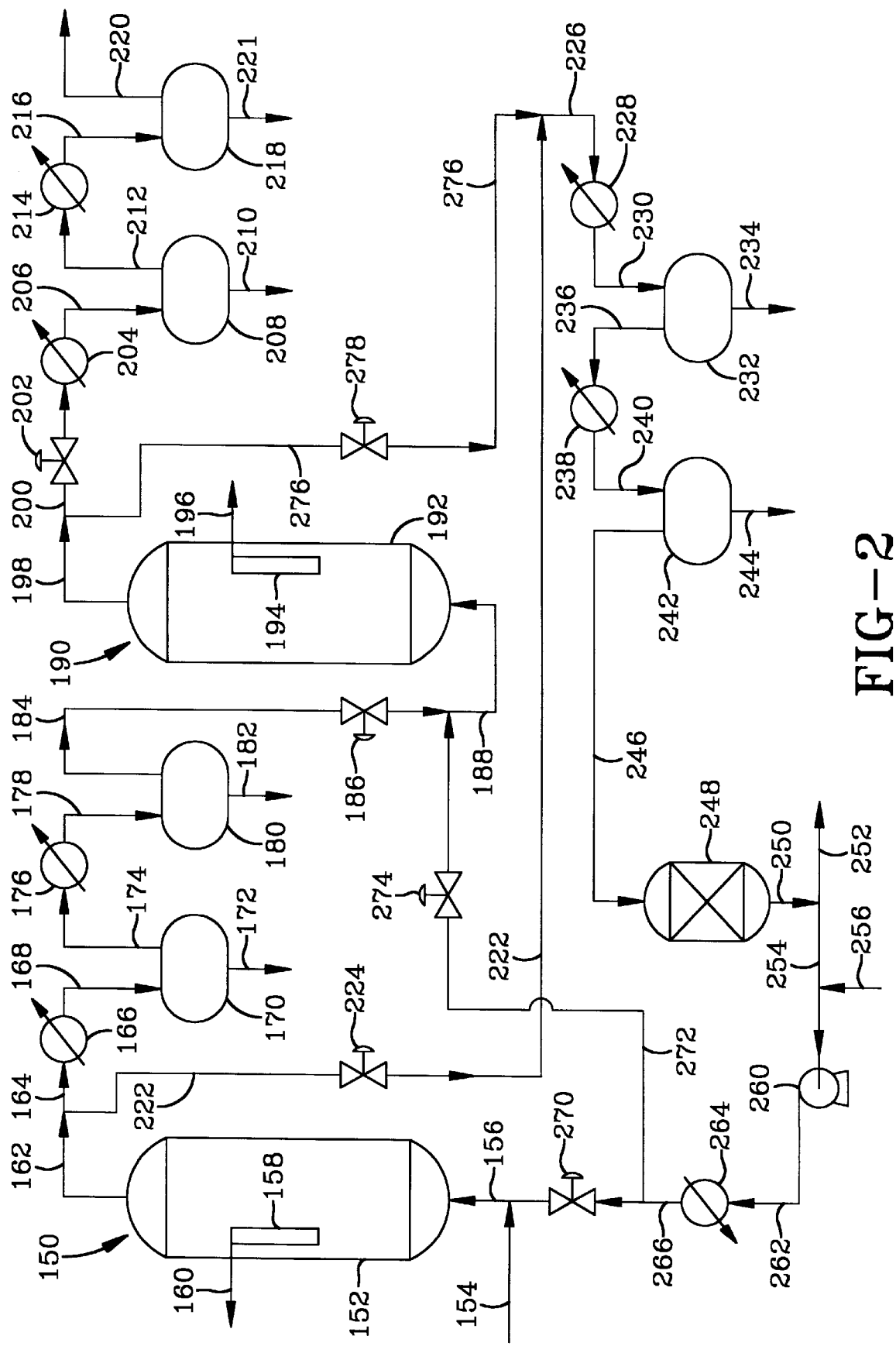
FIG. 2 is a box type schematic of an HCS process of the invention in which hot and cold separators are dedicated to rejuvenation.

FIG. 2 is a schematic block diagram of a two stage slurry hydrocarbon synthesis process according to another embodiment of the invention, in which the rejuvenating offgas is passed through heat exchangers, hot and cold separator drums and a water scrubber dedicated to the rejuvenation offgas cleanup. This is unlike the embodiment illustrated in FIG. 1 in which the hot and cold separators used for rejuvenation offgas cleanup is the same as that used for the HCS tail gas exiting the top of the reactors. The embodiment illustrated in FIG. 2 permits one set of hot and cold separators to be used for tail gas clean-up in more than one first stage reactor and another set for more than one second stage reactor, because the rejuvenation offgas clean up does not use the same hot and cold separators used for reactor tail gas. In this embodiment, as in the previous embodiment, CO flow into the HCS reactors is periodically stopped, CO purged from the slurry, rejuvenating gas passed up through the slurry to rejuvenate the catalyst and the CO flow into the slurry resumed. The first stage slurry reactor 150 comprises a cylindrical vessel 152 which contains an HCS slurry (not shown) within. A syngas feed line 154 passes a syngas comprising a mixture of $H_2$ and CO into line 156 which feeds the gas into the bottom of the reactor from where it is injected up into the bottom of the slurry as bubbles by suitable gas injection means (not shown) and reacts with the solid catalyst particles in the slurry liquid to form hydrocarbons, at least a portion of which are liquid at the reaction conditions. The liquid hydrocarbons are separated from the catalyst particles by suitable means, such as one or more filters either in the slurry in the reactor or in an outboard filtration vessel. In this particular embodiment, one or more liquid filters briefly illustrated as box 158 are immersed in the reactive slurry and the liquid hydrocarbon products are withdrawn from the reactor via line 160 and upgraded to more valuable products by fractionation and/or one or more conversion operations, or sold neat. This first stage reactor is operated at less than 100% conversion. Unreacted syngas and gas products of the HCS reaction pass up through the slurry into the top portion of the reactor and are withdrawn as tail gas via gas line 162. As is the case for the previous embodiment, the amount of syngas fed into the first stage reactor(s) and the CO conversion in the first stage is such as to insure sufficient unreacted syngas in the first stage tail gas to supply the feed gas requirements to the second stage, with little and preferably no syngas make-up from the syngas plant. The tail gas removed from the first stage reactor is passed, via lines 162 and 164, through a first stage hot heat exchanger 166 which cools the gas to condense out some of the water vapor and $C_{10}$–$C_{12+}$ hydrocarbons as liquids. The actual amounts and carbon numbers depend on the gas composition and the separator temperature and pressure. The mixture of condensed liquids and the remaining gas is passed via line 168 into separator 170 in which the liquid condensate is removed from the bottom via line 172, and the gas removed overhead via line 174. A typical temperature for this hot separator will be in the range of from about 200° to 300° F., with the pressure slightly lower than that in the reactor. The water and hydrocarbon reduced tail gas removed from separator 170 is passed via line 174 through a first stage cold heat exchanger 176 in which it is further cooled to condense most of the remaining water and heavier hydrocarbons from the gas, which are then passed into separator 180 via line 178. The water and hydrocarbon condensate is removed from the separator via line 182, with the substantially water and $C_{5+}$ reduced tail gas fed into the bottom of second stage slurry HCS reactor 190, via gas feed lines 184 and 188, in which it is bubbled up through the bottom of the HCS slurry (not shown) in the reactor, in a manner much the same as for the first stage reactor 150. A typical temperature and pressure for the second stage cold separator may be in the 50°–150° F. range at a pressure of about 200–600 psia., and the amount of water vapor remaining in the gas may be in the 0.2–0.5 mole % range. In reactor 190, the $H_2$ and CO containing tail gas contacts the catalyst particles in the slurry and most of the CO in the gas is converted into hydrocarbons, at least a portion of which are liquid at the reaction conditions. The second stage slurry reactor 190 also comprises a hollow outer shell 192 containing a three phase HCS slurry (not shown) and liquid filtration means 194 within for separating the liquid hydrocarbon products from the catalyst particles as filtrate, with the filtrate removed from the reactor via line 196 and upgraded into more valuable product by fractionation and/or one or more conversion operations, etc.. Second stage reactor 190 is also operated at less than 100% CO conversion, so that unreacted $H_2$ and CO exit the reactor, along with the gas products of the HCS reaction, as tail gas. The tail gas is removed overhead via gas lines 198 and 200 and passed through a first heat exchanger 204 in which it is cooled to condense out some of the water and $C_{4+}$ hydrocarbon products. The gas and liquid mixture is passed from 204 into a first separator 208, via line 206. The liquids are removed from the bottom of the separator via line 210, and the water and hydrocarbon reduced tail gas is passed via line 212 into a second heat exchanger 214 in which it is further cooled to condense most of the remaining water and heavier hydrocarbons out as liquids. The gas and liquid mixture is passed from heat exchanger 214 into a second separator 218 via line 216, in which the liquids settle out of the gas and are removed via line 221. The water and hydrocarbon reduced tail gas passes out of separator 218 via line 220 and may be used for a variety of purposes, such as fuel, recycle to syngas generation, used for catalyst rejuvenation, further cooled to recover hydrocarbons, etc.. Temperatures in the second stage hot and cold separators will typically range from about 200°–300° F. and 50°–150° F., respectively.

When the catalyst activity in the first stage reactor 10 falls below anywhere from 50–95%, but for the sake of this illustration, 90%, the syngas flow into the reactor is stopped by any suitable means, such as one or more valves (not shown) and purge gas comprising a mixture of $H_2$, and a diluent such as $N_2$, is passed up into and through the slurry in the reactor via lines 256, 254, 262, etc. and finally up through line 156. The purge gas may also be introduced through lines 154 and 156, entering line 154 from another line (not shown), etc. or any other convenient means. As discussed above under the Summary, other diluents such as $CH_4$ may also be used. All or a part of the purge gas may be a hydrogen rich hydroisomerization offgas (e.g., primarily $H_2$ and $CH_4$), or other suitable and available hydrogen containing process gas. In a once through purge mode, the hydrogen containing purge gas exits the reactor being purged which, in this embodiment is one of two or more first stage reactors of which only the one, 150, is shown, via line 162. Valve means 224 is open and a corresponding valve means in line 164 (not shown) is closed, so that the purge gas doesn't pass through the coolers and separators and into the second stage reactor(s). In this embodiment, the tail gas from the rest of the first stage reactors, which are still on-line producing hydrocarbons, is passed into and through the coolers and separators and into the second stage reactors without being diluted or contaminated by the purge gas from the first stage reactor being rejuvenated. The purge gas recovered from reactor 150 passes through lines 222 and 226 into the cooling, separating and water scrubbing unit illustrated in the Figure, and is removed from the system via line 252. During the purge, some of the CO remaining in the slurry is removed by reacting, in the presence of the catalyst, with the $H_2$ in the purge gas and some of it mixes with the diluent and is removed in that fashion. In a once-through purge, none of the CO removed from the slurry as overhead gas is returned back into the slurry. Consequently, in a once-through purge in which the purge gas is not recycled, the slurry may be completely purged of CO in five minutes or less. In a recycle purge mode of operation, the purge gas leaving the HCS reactor is passed via lines 162, 222 and 226 into the dedicated cooling, separating and scrubbing system for the recycle rejuvenating gas, in which it is also compressed by compressor 260 and fed back up into the reactor via lines 262, 266, 268 and 156. A recycle purge operating mode takes longer than a once-through purge (e.g., 30 min. instead of 5 min.), but reduces the amount of diluent and compressor duty required. To reduce build up of diluent during a recycle purge, a bleed line 252 enables removal of some of the purge gas being recycled and make-up hydrogen or a hydrogen containing gas is supplied, via line 256, to the recycled purge gas being fed back into the reactor. After at least most and preferably all of the CO in the slurry in the reactor(150) being purged is removed, a hydrogen containing catalyst rejuvenating gas is passed into the slurry in which it contacts the catalyst and rejuvenates it. Depending on the availability and composition, the same gas source may or may not be used for both the purge and rejuvenation. During the rejuvenation of the purged slurry, the rejuvenation offgas passes up and out of the reactor 150 via line 162 and then through lines 222 and 226 and into the dedicated rejuvenating gas clean-up unit comprising hot and cold heat exchangers and separators 228, 232, 238, 242 and gas scrubbing unit 248, in which the gas is scrubbed with water to remove remaining water removable products of the rejuvenation reaction. While rejuvenation may also be conducted in a once through mode, a recycle mode is preferred to conserve $H_2$ and reduce overall gas requirements. During the rejuvenation, water removable catalyst deactivating species are produced. Hence, the rejuvenation offgas is passed via lines 162, 222 and 226 into the gas cleanup unit. The offgas passes through hot and cold heat exchanger 228 and 238 and associated gas-liquid separators 232 and 242 in the same manner as for those associated with the HCS reactor tail gas and from there, into and through scrubber 248 via line 246. The heat exchangers cool the gas and most of the water and $C_{4+}$ hydrocarbons, along with oxygenates and water removable nitrogen species, are removed as liquid via lines 234 and 244. In scrubber 248, the offgas is contacted with water, such as the HCS process water, which further reduces the level of catalyst deactivating species to produce a clean gas. The clean offgas is passed into compressor 260 via lines 250 and 254, and from there back into the HCS reactor as rejuvenation gas via lines 262, 266 and 156. Make-up $H_2$, if needed, is supplied to the clean recycled rejuvenation gas via line 256 and may be $H_2$ or an $H_2$ containing gas. Heat exchanger 264 is optional and is used to preheat the rejuvenating gas and/or purge gas, if need be, to prevent the slurry temperature in the reactor from falling to a point from which it will be time consuming and costly to reheat the slurry so that hydrocarbon synthesis can be resumed after rejuvenation. Line 272 enables recycled rejuvenation gas to be introduced into a second stage reactor (190). Where more than one second stage reactor is used, hydrocarbon production continues in the other second stage reactor(s) while one of the second stage reactors is being rejuvenated. The second stage reactor rejuvenation offgas is passed via lines 198 and 276 into the gas clean-up system and recycled as for the first stage rejuvenation. Valves 270, 274, 202 and 278 permit isolation of the first stage reactor and gas clean-up system from the tail gas heat exchangers and gas-liquid separation operation, as well as HCS reactors on-line in hydrocarbon production. In one embodiment of the invention, tail gas from which much of the water and hydrocarbons have been removed, may be used as all or a part of the rejuvenating gas, provided that the $H_2$ to CO mole ratio in the rejuvenating gas entering up into the slurry in the reactor is greater than 3:1, preferably greater than 4:1 and still more preferable greater than 5:1 and also provided that the total CO content in the gas is less than 10 mole % and preferably less than 5 mole %. If the CO content of the tail gas is too high to permit this, then it can be passed through a water gas shift reactor, reforming unit, physical or chemical adsorption or absorption, and the like to reduce the CO content of the gas to below the maximum limit of 10 mole %. These units are not illustrated for the sake of convenience. Further, if tail gas is used for as all or part of the rejuvenating gas, it will have been cooled and preferably scrubbed with water to separate and remove most of the water and just about all of any catalyst deactivating species from the gas.

While these embodiments both employ two stages of hydrocarbon synthesis, the invention is not intended to be limited to two stages, but may be practiced with one, two and more than two stages. The use of one, two and more than two stages is known and appreciated by those skilled in the art. Using more than one stage permits greater flexibility and more overall CO conversion than can be obtained with only in one stage. Two or more stages of hydrocarbon synthesis also reduces the heat transfer burden encountered using only a single stage and spreads the heat removal of the exothermic hydrocarbon synthesis reaction over the two or more stages. This means that each stage can be run at conditions for optimum selectivity towards the desired products. It also reduces catalyst rejuvenation requirements primarily to the first stage. Depending on the plant design and desired products, the second stage is run at either a lower or a higher pressure than the first stage. If the second stage is run at a higher pressure, then a compressor is used to increase the pressure of the first stage tail gas fed into the second stage as feed gas. A higher second stage pressure can be used to at least partially make up for the lower reactant and higher concentration of inerts (primarily $CH_4$, $CO_2$ and $N_2$) in the feed gas. Further, while only a single reactor is shown in each Figure for each stage of the two stage embodiments, more than one reactor may be, and more typically will be, used for each stage. As an illustrative, but nonlimiting example, the first stage may employ three or more reactors and the second stage two or more reactors. This permits a reactor to be taken off line for maintenance and repairs without having to shut down the entire HCS process. Finally, although the above illustration is for a slurry HCS process, the invention is not intended to be so limited, but may also be practiced with fixed and fluid bed processes.

In an HCS process, liquid and gaseous hydrocarbon products are formed by contacting a syngas comprising a mixture of $H_2$ and CO with a suitable Fischer-Tropsch type HCS catalyst, under shifting or non-shifting conditions and preferably non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for rejuvenating reversibly deactivated catalyst particles in a three phase hydrocarbon synthesis slurry comprising said particles and gas bubbles containing $H_2$ and CO in a hydrocarbon slurry liquid into which a mixture of CO and $H_2$ is flowing, said process comprising stopping said CO flow into said slurry followed by passing a CO free purge gas and $H_2$ through said slurry to remove said CO and form a CO reduced slurry, and then passing an $H_2$ containing catalyst rejuvenating gas through said CO reduced slurry to at least partially rejuvenate said catalyst particles and form a rejuvenated catalyst slurry and rejuvenating offgas.

2. A process according to claim 1 wherein said rejuvenating gas comprises a hydrocarbon synthesis reactor tail gas in which the $H_2$ to CO ratio is greater than 3:1 and wherein the CO content less than 10 mole %.

3. A process according to claim 1 wherein said rejuvenating offgas contains unreacted $H_2$ and is recycled back into said slurry as all or a portion of said rejuvenating gas after being scrubbed with water to remove catalyst deactivating species.

4. A process according to claim 2 wherein at least a portion of said tail gas is scrubbed with water to remove said catalyst deactivating species after passing through said slurry and recycled back a slurry as rejuvenating gas.

5. A process according to claim 1 wherein at least a portion of said purge gas is recycled back into said slurry during said purge.

6. A process according to claim 2 wherein said rejuvenation is conducted in the presence of $CO_2$ in an amount sufficient to suppress a water gas shift reaction.

7. A slurry hydrocarbon synthesis process which comprises the steps of:
(a) passing a synthesis gas comprising a mixture of $H_2$ and CO into a hydrocarbon synthesis slurry in the presence of one or more catalyst deactivating species and a hydrocarbon synthesis catalyst at reaction conditions effective to form hydrocarbons from said gas, at least a portion of which are liquid at said reaction conditions, wherein said slurry comprises said catalyst and gas bubbles in a hydrocarbon slurry liquid comprising said liquid hydrocarbons, and wherein said species at least partially reversibly deactivate said catalyst and form a deactivated catalyst slurry during said reaction;
(b) stopping the flow of CO into said slurry;
(c) passing a purge gas and $H_2$ through said slurry to remove CO and form a CO reduced slurry in which said CO content is less than 10 mole % of said gas in said slurry;
(d) passing a catalyst rejuvenating gas comprising $H_2$ through said CO reduced slurry to at least partially rejuvenate said deactivated catalyst and form a rejuvenated catalyst slurry, and
(e) passing synthesis gas back into said rejuvenated slurry to produce hydrocarbons.

8. A process according to claim 7 wherein said purge gas contains said $H_2$ in step (c).

9. A process according to claim 7 wherein at least a portion of said purge gas passing through said slurry is recycled back into said slurry as purge gas.

10. A process according to claim 7 wherein at least a portion of said rejuvenating gas is recycled back into said slurry as rejuvenating gas after being scrubbed with water to remove catalyst deactivating species formed by said rejuvenation.

11. A process according to claim 7 wherein said rejuvenating gas comprises a hydrocarbon synthesis reactor tail gas from which a portion of the water vapor and liquid hydrocarbons have been removed and in which, if CO is present, it is present in an amount of less than 10 mole % of said gas and the $H_2$ to CO mole ratio is greater than 3:1.

12. A hydrocarbon synthesis process in which a synthesis gas comprising a mixture of $H_2$ and CO is passed into a hydrocarbon synthesis slurry in a slurry hydrocarbon synthesis reactor in the presence of one or more catalyst deactivating species and a hydrocarbon synthesis catalyst at reaction conditions effective to react said $H_2$ and CO and form hydrocarbons and a tail gas comprising a mixture of hydrogen, water vapor and vaporized hydrocarbon products of said reaction, wherein at least a portion of said hydrocarbons are liquid at said reaction conditions, wherein said slurry comprises said catalyst and gas bubbles in a hydrocarbon slurry liquid comprising said liquid hydrocarbons, wherein said species at least partially reversibly deactivate said catalyst and form a deactivated catalyst slurry during said reaction, and wherein said catalyst is rejuvenated in-situ in said slurry in said reactor by:
(a) periodically stopping the flow of said CO into said reactor and then passing a purge gas and $H_2$ into said reactor to reduce the CO level in the gas in said slurry to less than 10% and form a CO reduced slurry;
(b) passing a hydrogen containing rejuvenating gas into said CO reduced slurry for a time sufficient to at least partially rejuvenate said catalyst and form a rejuvenated slurry and an offgas which contains hydrogen and species which reversibly deactivate said catalyst, wherein said rejuvenating gas contains less than 10 mole % CO and the hydrogen to CO mole ratio is greater than 3:1, and
(c) restoring said CO flow into said rejuvenated slurry to again synthesize said hydrocarbons by reacting said CO with $H_2$ in said slurry, and wherein at least a portion of said rejuvenating gas comprises at least one of (i) said hydrogen containing synthesis reactor tail gas from which catalyst deactivating contaminants, most of the water and most of the $C_{4+}$ hydrocarbons have been removed and (ii) said hydrogen containing rejuvenating offgas from which said catalyst deactivated species have been removed.

13. A process according to claim 12 wherein said water and hydrocarbons are removed from said tail condensation.

14. A process according to claim 13 wherein said CO, if present in said mixture of purge gas and hydrogen present in an amount of less than 5 mole % and the $H_2$ to CO mole ratio is greater than 5:1.

15. A process according to claim 14 wherein said tail gas has been reduced in CO concentration prior to being used as rejuvenation gas.

16. A process according to claim 12 wherein rejuvenation gas contains less than 5 mole % CO and has a hydrogen to CO mole ratio greater than 5:1.

17. A process according to claim 12 wherein all or a portion of $C_{5+}$ hydrocarbons produced by said hydrocarbon synthesis process are upgraded to more valuable products by fractionation and/or a conversion operation.

18. A process according to claim 12 wherein said rejuvenation is conducted in the presence of $CO_2$ in an amount sufficient to suppress a water gas shift reaction.

19. A process according to claim 1 wherein all or a portion of $C_{5+}$ hydrocarbons produced by said hydrocarbon synthesis process are upgraded to more valuable products by fractionation and/or a conversation operation.

20. A process according to claim 7 wherein all or a portion of $C_{5+}$ hydrocarbons produced by said hydrocarbon synthesis process are upgraded to more valuable products by fractionation and/or a conversion operation.

* * * * *